United States Patent [19]

Wegmann

[11] Patent Number: 4,885,177
[45] Date of Patent: Dec. 5, 1989

[54] NATURAL CORN ROOTWORM CONTROL

[76] Inventor: Gary J. Wegmann, R.R. 2, Box 205, Earlville, Iowa 52041

[21] Appl. No.: 191,343

[22] Filed: May 9, 1988

[51] Int. Cl.$^4$ .................. A61K 35/78; A61K 35/60
[52] U.S. Cl. ...................... 424/95; 424/195.1; 424/DIG. 10; 514/919; 71/3
[58] Field of Search ............... 424/95, 195.1, DIG. 9, 424/DIG. 12, DIG. 10; 426/1; 514/75, 919; 71/79, 11

[56] References Cited

U.S. PATENT DOCUMENTS

| | | | |
|---|---|---|---|
| 1,489,940 | 4/1924 | Hiller | 71/11 |
| 3,050,383 | 8/1962 | Wilson | 71/11 |
| 4,535,077 | 8/1985 | Fahmy | 514/143 |
| 4,676,985 | 6/1987 | Gould et al. | 424/195.1 |

OTHER PUBLICATIONS

Mihaliak, C. et al. "Inhibition of feeding by a generalist insect due to increased volatile leaf terpenes under nitrate-limiting conditions" CA108: 34818m.
BeHolo, G. B. "Terpenes" in *Natural Products for Innovative Pest Management*, 1983 Pergamon Press, New York, pp. 204–206.
Fedeli, E. et al. "Minor components of the unsaponifiable fraction in different anatomical parts of the soy bean" CA66:35402x.
Reed et al. "Effects of two triterpenoids from neem on feeding by cucumber beetles (Coleoptena: chrysomelidas)" CA98:84856t.
Villani M. G. et al. "Laboratory bioassay of crude extracts as anti-feedants for the southern corn rootworm (Coleoptena: chrysomelidae)" BA81(2):12660.
Shaw, J. T. et al. "Corn Rootworm oriposition in Soybeans" BA66(4): 20474.

*Primary Examiner*—Ronald W. Griffin
*Assistant Examiner*—Jean C. Witz
*Attorney, Agent, or Firm*—Zarley, McKee, Thomte, Voorhees & Sease

[57] ABSTRACT

A whooly natural method of rootworm control which does not involve insecticides. The method comprises treating the ground surrounding seed corn with a small but rootworm controlling effective amount of a treating composition that contains a mixture of soybean meal and fish meal.

18 Claims, No Drawings

NATURAL CORN ROOTWORM CONTROL

BACKGROUND OF THE INVENTION

In areas where corn is one if not the most popular row crops, it is common knowledge that one of the gravest problems faced by the corn farmer is rootworms. Rootworms infest the fields in which corn is grown and use the roots of the corn plant as food. The rootworm often will cause severe damage to the root of a starting plant and stunt the plant's growth, significantly decreasing yield. Also, rootworm damage decreases the yield by causing a phenomenon known as lodging. Lodging is caused by the corn plant becoming weak at its base where the root spreads out into the soil. As the plant becomes heavier as it matures, it may begin leaning at an acute angle to the ground. This is particularly troublesome in areas that are susceptible to high winds. The high winds cause even more acute lodging, and in some cases may completely blow the plant over. As a result, with the plant leaning at a highly acute angle or perhaps completely blown over, it cannot be combined thus decreasing overall yield. Thus, it can be seen that rootworm is a common problem for corn fields.

The state of the art technology involves treating the field during planting with insecticides in order to inhibit rootworm. The problem of rootworm is especially acute in fields which are planted year after year with corn only, as opposed to rotating corn with other crops such as soybeans or alfalfa. Common insecticides applied during planting in order to effectively treat or inhibit rootworm are sold under the trademarks Difonate ®, Counter ® and Lorsban ®. Such chemical controls for rootworm increase the expense of corn crop somewhere between $8 and $12 per acre. Also, there are significant environmental problems that potentially exist with chemical insecticide treatment. For example, it is well known that insecticides may have some carcinogen effect, and may have a significant deleterious effect on ground water.

Thus, while it may be possible by chemical insecticide treatment to effectively control rootworm, the control itself has its own undesirable side effects, namely significantly increased cost per acre for planting of the crop, and the significant risk of pollution of ground water, and finally the hazard of handling chemical insecticides, some of which are known to be carcinogenic.

It therefore can be seen that there is a real and continuing need for an effective way of treating rootworm to inhibit rootworm by a wholly natural means which has little or no hazards for handling, which uses only natural nonpolluting ingredients, and which has a low cost per acre.

It is a primary objective of this invention to satisfy the above need.

SUMMARY OF THE INVENTION

This invention is premised on the discovery that rootworm control can occur with a treating composition of wholly naturally occurring non-ground-water polluting ingredients. The treating composition is a mixture of soybean meal and fish meal in one embodiment, and in another is soybean meal only. In a preferred means of application, the treatment composition is mixed with dry starter fertilizer, and both are applied during planting.

DETAILED DESCRIPTION OF THE INVENTION

This invention involves the discovery that rootworm can be effectively controlled by applying to the soil surrounding a planted seed a small but rootworm controlling effective amount of a treating composition which in its broadest sense is soybean meal, and which in a preferred embodiment is a combination of soybean meal and fish meal.

The soybean meal which is used as a starting material for preparing the treating composition of the present invention is well-known and is an available material. It can be obtained from any one of many well-known commercial suppliers. Briefly, it is prepared by extruding soybeans into a meal-like substance. The soybean meal contains both the fatty oils and the meal material. The meal material is largely carbohydrate and protein material, and the oil is largely triglyceride oils. These triglycerides can and may contain saturated or unsaturated long chain acyl radicals having from about 12 to about 22 carbon atoms. Characterization of the triglyceride oil content of soybean oil is well known and need not be described herein.

Where fish meal is used in combination with the soybean meal for the treating composition, the fish meal likewise is comprised of ground fish residue. This contains naturally occurring carbohydrate and protein material and fish oils which also are triglycerides but of animal origin.

The preferred treating composition of the present invention is a mixture of both soybean meal and fish meal, with the weight ratio of soybean meal to fish meal within the range of about 0.5:1 to about 4:1. Preferably the weight ratio of soybean meal to fish meal is from about 1:1 to about 3:1, and most preferably from about 1:1 to about 2:1 of soybean meal to fish meal.

These compositions are quite oily and for purposes of application to the field, it has been found most effective to mix these with conventional dry starter fertilizer such as phosphate fertilizer. When this is done, the total composition comprises the treating composition of soybean meal and/or fish meal and the dry starter fertilizer such as a conventional phosphate starter fertilizer. The total composition should comprise from about 3% by weight to about 15% by weight of the rootworm treating composition, and preferably from about 5% by weight to about 10% by weight of the rootworm treating composition. The dry mix total composition should be mixed to provide substantial homogeneity.

Thereafter, the total dry mix composition is simply applied to the field in the conventional manner that phosphate starter is applied at the time of planting. This conventional treatment involves opening a furrow alongside and beneath the seed furrow, applying the total dry composition, which includes the fertilizer to the furrow alongside the seed furrow, and depositing the seed in the seed furrow, at which time both furrows are closed.

Certain applications of the invention have been made using soybean meal only, but better results seem to occur when soybean meal and fish meal are used conjunctively.

It is not known precisely why the invention works, but in every instance where it has been applied, it has successfully controlled rootworm with little or no rootworm damage occurring. The cost of the composition of the present invention runs about $2 per acre compared with chemical insecticide control of about $8-$12 per acre.

In one field where the composition of the present invention was used, it was used in the following manner. Ten pounds of soybean meal was mixed with between 4 and 5 pounds of fish meal, and this was added to 175 pounds of conventional phosphate starter fertilizer. The mixture was mixed to provide homogeneity and substantial dryness, and then placed in a fertilizer box on a John Deere planter. The planter was moved through the field in a conventional manner. The furrow opened, the total treating composition was metered out into the bottom of the furrow, the seed planted, the furrow closed and thereafter the crop grown. No rootworm problems occurred. In comparison with another side-by-side field which was chemically treated with insecticide, there seemed to be no significantly different appearance. There was no difference in lodging between the two fields. In short, in all respects the treatments seemed equal.

It is not known whether the meal only, with the oil extracted might also work. It is a possibility, however, that the "active" is contained in the meal alone, as opposed to the triglyceride oil. Thus, it is contemplated as a part of this invention that extracted meal, apart from the triglyceride oils from both the soybean meal and the fish meal can be utilized.

It therefore can be seen that the invention accomplishes all of its stated objectives.

What is claimed is:

1. A method of rootworm control, which comprises: treating the ground surrounding seed corn with a small but rootworm controlling effective amount of a treating composition of soybean meal and fish meal which includes triglyceride oil.

2. The method of claim 1 wherein said treating composition has a weight ratio of soybean meal to fish meal of from about 0.5:1 to about 4:1.

3. The method of claim 2 wherein the weight ratio of soybean meal to fish meal is from about 1:1 to about 3:1.

4. The method of claim 3 wherein the weight ratio of soybean meal to fish meal is from about 1:1 to about 2:1.

5. The method of claim 1 wherein said treating occurs with a total composition which also contains dry starter fertilizer along with soil treating composition.

6. The method of claim 5 wherein the dry starter fertilizer is a phosphate starter fertilizer.

7. The method of claim 5 wherein said starter fertilizer is blended with said treating composition to provide substantial homogeneity of said total composition.

8. The method of claim 5 wherein said total composition comprises on a weight basis from about 3% by weight to 15% by weight of said treating composition.

9. The method of claim 5 wherein said total composition comprises on a weight basis from about 5% by weight to 10% by weight of said treating composition.

10. A method of rootworm control without use of insecticides, which comprises:
preparing a treating composition of soybean meal and fish meal which includes triglyceride oil;
mixing said treating composition with dry starter fertilizer to obtain a total composition; and
applying said total composition to the soil surrounding an area for seed corn planting.

11. The method of claim 10 wherein said treating composition has a weight ratio of soybean meal to fish meal of from about 0.5:1 to about 4:1.

12. The method of claim 11 wherein the weight ratio of soybean meal to fish meal is from about 1:1 to about 3:1.

13. The method of claim 12 wherein the weight ratio of soybean meal to fish meal is from about 1:1 to about 2:1.

14. A method of rootworm control in fields of corn, said method comprising:
opening a furrow for planting of seed corn;
treating the ground area of the furrow with a small but rootworm controlling effective amount of a treating composition of soybean meal which includes triglyceride oil; and
planting the seed in the treated furrow.

15. The method of claim 14 wherein said treating composition includes both soybean meal and fish meal.

16. The method of claim 14 wherein said treating composition is blended with dry starter fertilizer to provide a total composition.

17. The method of claim 16 wherein said treating composition includes fish meal.

18. The method of claim 10 wherein said total composition is mixed to comprise on a weight basis 3% by weight to 15% by weight of treating composition.

* * * * *